United States Patent [19]

Toja et al.

[11] Patent Number: 4,885,307
[45] Date of Patent: Dec. 5, 1989

[54] DERIVATIVES OF 1-ARYLSULPHONYL-1,5-DIHYDRO-2H-PYRROL-2-ONE, AND COMPOSITIONS CONTAINING THEM

[75] Inventors: Emilio Toja; Carlo Gorini, both of Milan; Fernando Barzaghi; Giulio Galliani, both of Monza, all of Italy

[73] Assignee: Roussel Uclaf, Paris, France

[21] Appl. No.: 205,958

[22] Filed: Jun. 13, 1988

[30] Foreign Application Priority Data

Jun. 24, 1987 [IT] Italy .................................. 21029 A/87

[51] Int. Cl.$^4$ ..................... C07D 207/38; D61K 31/40
[52] U.S. Cl. .................................. 514/425; 548/542
[58] Field of Search ................. 548/542, 545; 514/425

[56] References Cited

U.S. PATENT DOCUMENTS

| | | | |
|---|---|---|---|
| 3,117,975 | 1/1964 | Bortnick et al. | 548/545 |
| 3,423,426 | 1/1969 | Kohn | 548/542 |
| 3,686,169 | 8/1972 | Coran et al. | 548/542 |

FOREIGN PATENT DOCUMENTS

| | | |
|---|---|---|
| 0138721 | 4/1985 | European Pat. Off. |
| 3637507 | 5/1988 | Fed. Rep. of Germany ...... 548/544 |

OTHER PUBLICATIONS

Drugs of the Future, vol. 10, No. 12, 1985, pp. 972, 974.

*Primary Examiner*—David B. Springer
*Attorney, Agent, or Firm*—Stevens, Davis, Miller & Mosher

[57] ABSTRACT

Compounds useful in the treatment of patients suffering from intellectual or nervous asthenias, memory failures, senescence or mental strain of the formula (I)

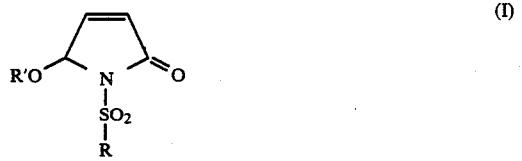

in which R' represents hydrogen, a linear, branched or cyclic alkyl containing up to 8 carbon atoms, alkenyl containing from 2 to 8 carbon atoms, acyl containing from 1 to 6 carbon atoms or aralkyl containing from 7 to 15 carbon atoms and R represents aryl containing up to 14 carbon atoms, possibly substituted, or a mono- or polycyclic heterocyclic aromatic radical, possibly substituted; also thereapeutic compositions containing those compounds and method of use.

7 Claims, No Drawings

DERIVATIVES OF 1-ARYLSULPHONYL-1,5-DIHYDRO-2H-PYRROL-2-ONE, AND COMPOSITIONS CONTAINING THEM

This invention relates to new derivatives of 1-arylsulphonyl-1,5-dihydro-2H-pyrrol-2-one, the process and intermediates for their preparation, their use as medicaments and the compositions containing them.

The subject of the invention is the compounds of the general formula (I):

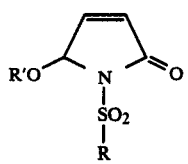
(I)

in which R' represents hydrogen, a linear, branched or cyclic alkyl containing up to 8 carbon atoms, alkenyl containing from 2 to 8 carbon atoms, acyl containing from 1 to 6 carbon atoms or aralkyl containing from 7 to 15 carbon atoms and R represents aryl containing up to 14 carbon atoms, possibly substituted, or a mono- or polycyclic heterocyclic aromatic radical, possibly substituted.

As alkyl, there is preferred an alkyl containing from 1 to 6 carbon atoms, for example, methyl, ethyl, n-propyl, isopropyl, n-butyl, isobutyl, tertbutyl, n-pentyl, n-hexyl, cyclopropyl, cyclobutyl, cyclopentyl or cyclohexyl.

As alkenyl, there is preferred ethenyl, propenyl or butenyl.

As acyl, there is preferred acetyl, propionyl or butyryl.

As aralkyl, there is preferred phenalkyl.

As aryl, there is preferred phenyl or naphthyl.

As the heterocyclic radical, there is preferred one of the following radicals: thienyl, furyl, pyranyl, pyridyl, benzofuranyl, isobenzafuranyl, chromanyl, isochromanyl, chromenyl, xanthenyl, phenoxathienyl, oxazolyl, isoxazolyl, furazanyl, phenoxazinyl, thieno[2,3-b]furanyl, 2H-furo[3,2-b]pyranyl, benzoxazolyl or morpholinyl.

When R is substituted, it carries preferably as substituents one or more substituents chosen from the group constituted by the free, esterified or etherified hydroxy radical in which the ester or ether part contains from 1 to 18 carbon atoms, such, for example, as acetoxy, methoxy or benzyloxy, the ketone and oxime functions, linear, branched or cyclic, saturated or unsaturated alkyl including up to 18 carbon atoms, for example methyl, ethyl, propyl or isopropyl, ethenyl or ethynyl, halogen such as fluorine, chlorine or bromine, the groups $CF_3$, $SCF_3$, $OCF_3$, $NO_2$, $NH_2$ or $C\equiv N$, phenyl, the acyl or alkoxycarbonyl groups containing from 2 to 8 carbon atoms and the alkylsulphonyl groups containing from 1 to 6 carbon atoms.

The invention has as its subject the compounds with the formula (I) in which R represents possibly substituted phenyl.

The invention also has particularly as its subject the compounds with the formula (I) in which R' represents a linear, branched or cyclic alkyl containing up to 8 carbon atoms and more particularly n-butyl or n-pentyl.

Quite specially the subject of the invention is 1-benzene-sulphonyl-1,5-dihydro-5-n-butoxy-2H-pyrrol-2-one, 1-benzene-sulphonyl-1,5-dihydro-5-n-pentyloxy-2H-pyrrol-2-one and 1-(3-trifluoromethyl-benzenesulphonyl)-1,5-dihydro-5-n-butoxy-2H-pyrrol-2-one.

The invention compounds present interesting pharmacological properties. They retard the extinction of the conditioned avoidance response, they retard the disappearance of the learned response, and they favor attention, vigilance and memorizing.

Therefore, a subject of the invention is the products with the formula (I), as medicaments, useful in particular in the treatment of intellectual or nervous asthenias, memory failures, senescence, and mental fatigue.

The subject of the invention, as medicaments, is more particularly the preferred compounds mentioned previously and notably the compounds of Examples 4, 6 and 12.

The usual daily dose is variable according to the affection concerned, the subject treated and the administration route. It can be between 0.7 mg and 40 mg/kg for example, between 2 and 20 mg/kg in one or more doses for the product of Example 4 administered by oral route.

The subject of the present invention is also the pharmaceutical compositions containing as active principle at least one compound with the formula (I).

The pharmaceutical compositions of the invention can be solid or liquid, and are presented in the pharmaceutical forms currently used in human medicine, such as, for example, plain or sugar-coated tablets, capsules, granules, suppositories and injectable preparations; they are prepared according to the usual methods.

The active principle or principles can be incorporated with the excipient usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents, and preservatives.

Also a subject of the invention is a process for the preparation of compounds with the formula (I), characterized in that the 1,5-dihydro-5-hydroxy-2H-pyrrol-2-one of the formula:

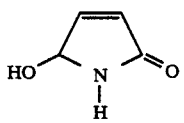

is submitted to the action of an alcohol with the formula (II):

R'OH     (II)

R' being as previously defined, in order to obtain the compound with the formula (III):

(III)

which is submitted to the action of a compound with the formula (VI):

RSO$_2$—Hal     (IV)

in which Hal represents chlorine or bromine and R retains its previous significance, in order to obtain the corresponding compound with the formula (I).

In a preferred method the condensation of the 1,5-dihydro-5-dihydroxy-2H-pyrrol-2-one and the alcohol of formula (II) takes place in the presence of Amberlite resin.

the condensation between the product with the formula (III) and the product with the formula (IV) is effected:

(a) in the presence of a strong base such as butyllithium, an alkaline hydride such as sodium hydride or sodium bis-(trimethylsilyl)amide;

(b) in a solvent chosen from the group constituted by tetrahydrofuran, benzene, dimethylformamide, dimethylsulphoxide or the diethyl ether of diethylene glycol.

The 1,5-dihydro-5-hydroxy-2H-pyrrol-2-one is a product described in Synthesis 1973, p. 167.

The compounds of formula (III) are new products and are themselves one of the subjects of the present invention as new chemical compounds.

The following examples illustrate the invention without, however, limiting it.

EXAMPLE 1:

1-benzenesulphonyl-1,5-dihydro-5-ethoxy-2H-pyrrol-2-one.

Stage A: 1,5-dihydro-5-ethoxy-2H-pyrrol-2-one.

A mixture of 2.3 g of 1,5-dihydro-5-hydroxy-2H-pyrrol-2-one in 140 cm$^3$ of ethanol and 100 g of Amberlite resin IR-120 (H) is taken to reflux for 30 minutes. After allowing to cool, filtering off the resin and distilling the ethanol off under reduced pressure, 2.76 g of the expected product is obtained, m.p. 50°–52° C.

Stage B: 1-benzenesulphonyl-1,5-dihydro-5-ethoxy-2H-pyrrol-2-one.

7.37 cm$^3$ of a 1.6M solution of n-butyllithium in n-hexane is added to a solution of 1.5 g of 1,5-dihydro-5-ethoxy-2H-pyrrol-2-one in 40 cm$^3$ of tetrahydrofuran cooled to −35° C., operating at −35°/−30° C. The mixture is agitated for 20 minutes, then cooled to −40° C., and while maintaining the temperature between −38° C. and −40° C., a solution is added of 2.08 g of benzene sulphonyl chloride in 10 cm$^3$ of tetrahydrofuran. The temperature is allowed to return to the ambient, the solvent is evaporated under reduced pressure, and the residue is chromatographed on silica (eluent: ethyl acetate-n-hexane, 1—1). 1.15 g of the expected product is obtained. m.p. 117°–119° C., crystallized from ethyl ether.

EXAMPLE 2:

1-benzenesulphonyl-1,5-dihydro-5-n-propyloxy-2H-pyrrol-2-one.

Stage A: 1,5-dihydro-5-n-propyloxy-2H-pyrrol-2-one.

A mixture of 3 g of 1,5-dihydro-5-n-hydroxy-2H-pyrrol-2-one in 60 cm$^3$ of n-propanol and 1.5 g of Amberlite IR 120 H is taken to 60° C. for two hours 30 minutes. It is then allowed to cool, is filtered, evaporated to dryness and chromatographed on silica (eluent: ethyl acetate). 3.3 g of the expected product is obtained which is utilized as it is for the following stage.

Stage B: 1-benzenesulphonyl-1,5-dihydro-5-n-propyloxy-2H-pyrrol-2-one.

To a solution of 3 g of 1,5-dihydro-5-n-propyloxy-2H-pyrrol-2-one, in 80 cm$^3$ of tetrahydrofuran, cooled to −45° C., there is added 13.25 cm$^3$ of a 1.6M solution of N-butyllithium in n-hexane, while maintaining the temperature between −35° and −45° C. After 30 minutes, a solution of 3.74 g of benzenesulphonyl chloride in 12 cm$^3$ of tetrahydrofuran is added at a temperature between −45° and −35° C., then the temperature is allowed to return to the ambient over two hours, followed by evaporating to dryness and chromatographing on silica (eluent: ethyl acetate-n-hexane, 1—1). 2.2 g of the expected product is recovered. m.p. 56°–58° C., crystallized from a mixture of ethyl ether-n-hexane, 1-2. By crystallizing from isopropanol, 1.4 g of the expected product is obtained, m.p. 66°–67° C.

EXAMPLE 3:

1-benzenesulphonyl-1,5-dihydro-5-isopropyloxy-2H-pyrrol-2-one.

Stage A: 1,5-dihydro-5-isopropyloxy-2H-pyrrol-2-one.

A mixture of 3 g of 1,5-dihydro-5-hydroxy-2H-pyrrol-2-one, 1.5 g of Amberlite IR 120 H and 60 cm$^3$ of isopropanol is taken to 45°–50° C. for 3 hours. After cooling, filtering and evaporating to dryness, 1.8 g of the expected product is obtained, m.p. 79°–81° C., crystallized from isopropanol.

Stage B: 1-benzenesulphonyl-1,5-dihydro-5-isopropyloxy-2H-pyrrol-2-one.

To a solution of 3 g of the product obtained at stage A in 80 cm$^3$ of tetrahydrofuran, there is added at −45° C., 13.2 cm$^3$ of a 1.6M solution of n-butyllithium in hexane, while maintaining the temperature between −45° C. and −40° C. After agitating for 30 minutes, a solution of 3.74 g of benzenesulphonyl chloride in 12 cm$^3$ of tetrahydrofuran is added, while maintaining the temperature at −45° to −40° C. The temperature is allowed to return to the ambient over 2 hours, followed by evaporating to dryness, taking up with 50 cm$^3$ of water and filtering, so obtaining 1.65 g of the expected product. m.p. 148°–149° C., crystallized from isopropanol.

EXAMPLE 4:

1-benzenesulphonyl-5-n-butoxy-1,5-dihydro-2H-pyrrol-2-one.

Stage A: 5-n-butoxy-1,5-dihydro-2H-pyrrol-2-one.

A mixture of 2.5 g of 1,5-dihydro-5-hydroxy-2H-pyrrol-2-one in 75 cm$^3$ of 1-butanol and 1.3 g of Amberlite IR 120 H is heated to 70° C. for 2 hours. After allowing to return to ambient temperature, the residue is filtered and the solvent is evaporated under reduced pressure. 3.9 g of the expected product is obtained.

Stage B: 1-benzenesulphonyl-5-n-butoxy-1,5-dihydro-2H-pyrrol-2-one.

15.7 cm$^3$ of a 1.6M solution of n-butyllithium in n-hexane is added to a solution of 3.9 g of the product obtained at stage A in 80 cm$^3$ of tetrahydrofuran, cooled, to −35° C., while keeping the temperature between −35° and −30° C. and agitating for 20 minutes. Then, at −40°/−38° C., there is added a solution of 4.44 g of benzenesulphonyl chloride in 20 cm$^3$ of tetrahydrofuran. The temperature is allowed to return to the ambient, the solvent is evaporated under reduced pressure and the residue is chromatographed on silica (eluent: n-hexane-ethyl acetate, 2-1). 1.9 g of the expected product is obtained, m.p. 66°–67° C., crystallized from isopropyl ether.

EXAMPLE 5:

1-benzenesulphonyl-1,5-dihydro-5-isobutyloxy-2H-pyrrol-2-one.

Stage A: 1,5-dihydro-5-isobutyloxy-2H-pyrrol-2-one.

A mixture of 3 g of 5-hydroxy-2H-pyrrol-2-one and 1.5 g of Amberlite IR 120 H in 60 cm$^3$ of isobutanol, is heated to 50° C. for 3 hours, then cooled and filtered, and the solvent is evaporated. After chromatographing the residue on silica (eluent: ethyl acetate), 4 g of the expected product is obtained.

Stage B: 1-benzenesulphonyl-1,5-dihydro-5-isobutyloxy-2H-pyrrol-2-one.

13.2 cm$^3$ of a 1.6M solution of n-butyllithium in hexane is added to a solution cooled to −45° C. of 3.3 g of 1,5-dihydro-5-isobutyloxy-2H-pyrrol-2-one obtained at stage A, in 80 cm$^3$ of tetrahydrofuran. The mixture is agitated for 30 minutes at −45° C./−40° C., then a solution of 3.74 g of benzenesulphonyl chloride in 12 cm$^3$ of tetrahydrofuran is added. The temperature is allowed to return to the ambient over 2 hours. After evaporating to dryness, the residue is chromatographed on silica (eluent: ethyl acetate-n-hexane, 1—1), and 1.7 g of the expected product is obtained. m.p. 82°-83° C., crystallized from isopropanol.

EXAMPLE 6:

1-benzenesulphonyl-1,5-dihydro-5-n-pentyloxy-2H-pyrrol-2-one.

Stage A: 1,5-dihydro-5-n-pentyloxy-2H-pyrrol-2-one.

A mixture of 3 g of 1,5-dihydro-5-hydroxy-2H-pyrrol-2-one in 60 cm$^3$ of n-pentyl alcohol and 1.5 g of Amberlite IR 120 H is heated to 50° C. for 3 hours. The temperature is allowed to return to the ambient, and after filtering, the solvent is distilled off under reduced pressure. The residue is distilled at 20° C. under 0.08 mbar. 3.8 g of the expected product is obtained, utilized as it is for the following stage.

Stage B: 1-benzenesulphonyl-1,5-dihydro-5-n-pentyloxy-2H-pyrrol-2-one.

13.8 cm$^3$ of a 1.5M solution of n-butyllithium in hexane is added at −45° C./−40° C. to a solution at −45° C. of 3.5 g of the product obtained at stage A in 80 cm$^3$ of tetrahydrofuran. After 30 minutes, a solution of 3.66 g of benzyl chloride in 12 cm$^3$ of tetrahydrofuran is added at −45° C./−40° C. The temperature is allowed to return to the ambient over 2 hours, and after evaporating to dryness, the residue is chromatographed on silica (eluent: ethyl acetate-n-hexane, 1—1). 2.5 g of the expected product is obtained.

EXAMPLE 7:

1-benzenesulphonyl-1,5-dihydro-5-n-hexyloxy-2H-pyrrol-2-one.

Stage A: 1,5-dihydro-5-n-hexyloxy-2H-pyrrol-2-one.

A mixture of 2.5 g of 1,5-dihydro-5-hydroxy-2H-pyrrol-2-one in 75 cm$^3$ of 1-hexanol and 1.3 g of Amberlite IR 120 H is heated to 85° C. for 2 hours. After allowing to cool to ambient temperature, the resin is filtered off and the solvent is evaporated under reduced pressure. The residue is distilled, and 3.4 g of the expected product is obtained. b.p. 120°-125° C. under 0.4 mbar.

Stage B: 1-benzenesulphonyl-1,5-dihydro-5-n-hexyloxy-2H-pyrrol-2-one.

39.37 cm$^3$ of a 1.4M solution of n-butyllithium in n-hexane is added to a solution of 10.1 g of 1,5-dihydro-5-n-hexyloxy-2H-pyrrol-2-one obtained at stage A in 170 cm$^3$ of tetrahydrofuran cooled to −30° C. The temperature is maintained at −30° C. while agitating for 15 minutes, then is reduced to −35° C. and a solution of 9.73 g of benzenesulphonyl chloride in 70 cm$^3$ of tetrahydrofuran is added, while maintaining the temperature at between −35° C. and −53° C. The temperature is allowed to return to the ambient, the solvent is evaporated under reduced pressure, and the residue is chromatographed on silica (eluent: ethyl acetate-n-hexane, 1-2). 5.68 g of the expected product is obtained.

EXAMPLE 8:

1-benzenesulphonyl-1,5-dihydro-5-cyclopentyloxy-2H-pyrrol-2-one.

Stage A: 1,5-dihydro-5-cyclopentyloxy-2H-pyrrol-2-one.

A mixture of 4.5 g of 1,5-dihydro-5-hydroxy-2H-pyrrol-2-one, 100 cm$^3$ of cyclopentanol and 2.25 g of Amberlite IR 120 H is maintained for 8 hours at 60° C. It is then allowed to cool, is filtered, and evaporated to dryness. The residue is chromatographed on silica (eluent: ethyl acetate-n-hexane, 1—1). 3 g of the expected product is obtained, m.p.=77°-78° C. crystallized from cyclohexane. After recrystallizing from a mixture of isopropyl ether-n-hexane, 1—1, m.p.=81°-82° C.

Stage B: 1-benzenesulphonyl-1,5-dihydro-5-cyclopentyloxy-2H-pyrrol-2-one.

15 cm$^3$ of a 1.6M solution of butyllithium in hexane is added at −40° C. to a solution cooled to −40° C. of 4 g of the product obtained at stage A in 160 cm$^3$ of tetrahydrofuran. After 30 minutes at −40° C., a solution of 4.2 g of benzenesulphonyl chloride in 30 cm$^3$ of tetrahydrofuran is added, and after allowing the temperature to return to the ambient, evaporating to dryness, and taking up the residue with a mixture of water and isopropyl alcohol (1-3), 2.06 g of the expected product is obtained, m.p. 123°-124° C.

EXAMPLE 9:

1-benzenesulphonyl-1,5-dihydro-5-cyclohexyloxy-2H-pyrrol-2-one.

Stage A: 1,5-dihydro-5-cyclohexyloxy-2H-pyrrol-2-one.

A mixture of 5 g of 1,5-dihydro-5-hydroxy-2H-pyrrol-2-one in 150 cm$^3$ of cyclohexane with 2.5 g of Amberlite IR 120 H is heated to 90° C. for 3 hours. After filtering, evaporating the solvent under reduced pressure and chromatographing the residue on silica (eluent: ethyl acetate-n-hexane, 1—1), 4.98 g of the expected product is obtained. m.p. 65°-66° C.

Stage B: 1-benzenesulphonyl-1,5-dihydro-5-cyclohexyloxy-2H-pyrrol-2-one.

To a solution of 2 g of 1,5-dihydro-5-cyclohexyloxy-2H-pyrrol-2-one, obtained at stage A in 35 cm$^3$ of tetrahydrofuran cooled to −40° C., 8.83 cm$^3$ of a 1.25M solution of n-butyllithium in hexane is added, while maintaining the temperature at −40° C./−35° C. After agitating for 20 minutes then cooling to −45° C., a solution of 1.95 g of benzenesulphonyl chloride in 15 cm$^3$ of tetrahydrofuran is added. The temperature is allowed to return to the ambient, the solvent is evaporated under reduced pressure, and the residue is chromatographed on silica (eluent: n-hexane-ethyl acetate, 3-1). 1 g of the expected product is obtained, m.p. 104°-106° C., crystallized from isopropyl ether.

EXAMPLE 10:

1-benzenesulphonyl-1,5-dihydro-5-benzyloxy-2H-pyrrol-2-one.

Stage A: 1,5-dihydro-5-benzyloxy-2H-pyrrol-2-one.

A mixture of 8 g of 1,5-dihydro-5-hydroxy-2H-pyrrol-2-one in 130 cm³ of benzyl alcohol and 4 g of Amberlite IR 120 H is heated for 3 hours at 60° C. The benzyl alcohol is distilled off at 65° C. under 0.3 mbar. then is drawn off under azeotropic form first with water and then with benzene. 13.6 g of the expected product is obtained, which is unstable on distilling.

Stage B: 1-benzenesulphonyl-1,5-dihydro-5-benzyloxy-2H-pyrrol-2-one.

To a solution of 1.83 g of sodium bis-trimethylsilylamide in 91 cm³ of ethyl ether, there is added a solution of 1.7 g of the product obtained at stage A in 4 cm³ of ethyl ether. The mixture is agitated for 30 minutes, then cooled to 0° C. and a solution of 1.51 g of benzenesulphonyl chloride in 5 cm³ of ethyl ether is added. The whole is agitated for 2 hours at ambient temperature, then poured into 50 cm³ of chloroform, filtered and evaporated. The residue is chromatographed on silica (eluent: ethyl acetate-n-hexane, 1—1). 0.7 g of the expected product is obtained, m.p. 56°-58° C.

EXAMPLE 11:

1-(4-methoxy-benzenesulphonyl)-5-n-butyloxy-1,5-dihydro-2H-pyrrol-2-one.

To a solution of 3 g of 5-n-butyloxy-1,5-dihydro-2H-pyrrol-2-one, obtained as in stage A of example 4, in 90 cm³ of tetrahydrofuran, there is added at $-70°$ C./$-65°$ C., 12.06 cm³ of a 1.6M solution of butyllithium in n-hexane. After agitating for 15 minutes at $-70°$ C., a solution of 4 g of 4-methoxy-benzenesulphonyl chloride in 12 cm³ of tetrahydrofuran is added at a temperature between $-70°$ C. and $-65°$ C. The temperature is allowed to return to the ambient over 2 hours, then, by evaporating to dryness and chromatographing the residue (eluent: ethyl acetate-n-hexane, 1—1), 1.6 g of the expected product is obtained. M.p. 65°-66° C., crystallized from isopropyl ether.

Analysis: $C_{15}H_{19}NO_5S$.

Calculated: C% 55.37 H% 5.89 N% 4.3 Found: 55.48 5.82 4.39.

EXAMPLE 12:

1-(3-trifluoromethyl-benzenesulphonyl)-5-n-butyloxy-1,5-dihydro-2H-pyrrol-2-one.

The operation is done as in example 11, using 3 g of the product obtained as at stage A of example 4 and by operating with 4.72 g of 3-trifluoromethyl-benzenesulphonyl chloride instead of with 4-methoxybenzenesulphonyl chloride. After distilling at 200° C. under 0.05 mbar, 1.6 g of the expected product is obtained, m.p. 42°-43° C.

Analysis: $C_{15}H_{16}F_3NO_4S$. Calculated: C% 49.58 H% 4.44 N% 3.85 Found: 49.71 4.43 3.82.

EXAMPLE 13:

1-(4-diphenylsulphonyl)-5-n-butyloxy-1,5-dihydro-2H-pyrrol-2-one.

The operation is done as in example 11, using 3 g of the product obtained as at stage A of example 4 and 4.88 g of 4-diphenylsulphonyl chloride instead of 4-methoxy-benzenesulphonyl chloride. 1.7 g of the expected product is obtained. m.p. 112°-114° C., crystallized from isopropyl alcohol.

Analysis: $C_{20}H_{21}NO_4S$. Calculated: C% 64.67 H% 5.70 N% 3.77 Found: 64.44 5.62 3.68.

EXAMPLE 14:

1-(4-nitrobenzenesulphonyl)-5-n-butyloxy-1,5-dihydro-2H-pyrrol-2-one.

The operation is done as in example 11, using 3 g of the product obtained as at stage A of example 4 and 4.5 g of 4-nitrobenzenesulphonyl chloride instead of 4-methoxy-benzenesulphonyl chloride. 2.7 g of the expected product is obtained. m.p. 88°-89° C. crystallized from isopropyl alcohol.

Analysis: $C_{14}H_{16}N_2OS$. Calculated: C% 49.40 H% 4.74 N% 8.23 Found: 49.37 4.85 8.32

EXAMPLE 15:

1-(2-thiophenesulphonyl)-5-n-butyloxy-1,5-dihydro-2H-pyrrol-2-one.

The operation is done as in example 11, using 3 g of the product obtained as at stage A of example 4 and 3.5 g of 2-thiophenesulphonyl chloride instead of 4-methoxy-benzenesulphonyl chloride. 0.3 g of the expected product is obtained. m.p. 56°-57° C., crystallized from isopropyl alcohol.

Analysis: $C_{12}H_{15}NO_4S_2$. Calculated: C% 47.82 H% 5.02 N 4.65 Found: 47.63 5.18 4.78

EXAMPLE 16:

1-(2-pyridinesulphonyl)-5-n-butyloxy-1,5-dihydro-2H-pyrrol-2-one.

To a solution of 6 g of 5-n-butyloxy-1,5-dihydro-2H-pyrrol-2-one obtained as at stage A of example 4 and 180 cm³ of tetrahydrofuran, there is added at $-70°$ C./$-65°$ C., 24.2 cm³ of 1.6M solution of n-butyllithium in hexane. After 15 minutes, there is added 100 cm³ of an ethereal solution of 2-pyridylsulphonyl chloride at $-70°$ C./$-65°$ C. This is allowed to return to ambient temperature over 2 hours and then evaporated to dryness. The residue is taken up with water, the solvent is decanted and the remainder is treated with isopropyl alcohol. 2.9 g of the expected product is obtained, m.p. 74°-75° C. A recrystallizing from isopropyl alcohol, 1.8 g of the expected product is obtained, m.p. 76°-77° C.

Analysis: $C_{13}H_{16}N_2O_4S$. Calculated: C% 52.68 H% 5.44 N% 9.45 Found: 52.28 5.31 9.33

Examples of pharmaceutical compositions.

(a) Tablets of the following formula were prepared:
Product of Example 4: 100 mg
Excipient q.s. for a tablet finished at: 300 mg (Detail of excipient: lactose, corn starch, treated starch, rice starch, magnesium stearate, talc).

(b) Capsules of the following formula were prepared:
Product of Example 6: 200 mg
Excipient q.s. for a capsule finished at: 300 mg (Detal of excipient: talc, magnesium stearate, aerosil).

PHARMACOLOGICAL STUDY

Acute toxicity and behaviour.

There were used male mice (Charles Rivers CD₁) weighing 22-23 g, without food for 16 hours. The products were administered to them normally by oral route at doses of 1000-500-250 mg/kg.

The effect of the products on the behaviour of the animals was evaluated according to the method described by Irvin [Psychopharmacologia (1968), 13, 222-257] during the first 8 hours and on the 24th hour.

The mortality was noted during the 7 days following the treatment.

The LD$_{50}$ was thus found to be greater than 1000 mg/kg on the products of Examples 1, 3 to 9 and 11 to 14.

Learning and memorizing.

There were used male mice (Charles Rivers CD$_1$) weighing 25–30 g. The animals were placed in the luminous part of a box with two compartments communicating by an opening [F. Barzaghi and G. Galliani, Brit. J. Pharmacol. 86, p. 661 (1985)].

At the instant when the mouse passes from the luminous compartment to the dark compartment, the opening closes and it is immediately punished by an electric discharge to the paws. The animal submitted to this procedure learns to memorize the punishment. In fact, if it is put back in the luminous compartment, it will thus avoid crossing the opening and reentering the dark compartment.

In order to induce a retrograde amnesia, the animals are submitted immediately after learning to an electric shock. After the electric shock, the products are administered by oral route at different doses.

There were used from 10 to 50 animals per dose.

The anti-amnesiac effect of the products is evaluated 3 hours after the treatment, using the same procedure as that utilized for the acquisition.

The time taken by the animal to return to the dark chamber (time limit 180 seconds) is used as evaluation parameter.

In the same experimental conditions, the control animals enter with a time lapse of 40–50 seconds.

The active products are those which cause a significant increase in the latency time with a bell-shaped dose-response curve.

The results are expressed as percentages of the increase of the latency time in comparison with the corresponding controls.

The following are the results:

| Product of example | Percentage increase in latency time in comparison with the controls | | |
|---|---|---|---|
| | Dose mg/kg per os | | |
| | 200 | 100 | 50 |
| 4 | 79* | 96* | 54* |
| 6 | 76* | 92* | 73* |
| 12 | 92* | 75* | 20* |

-continued

| Product of example | Percentage increase in latency time in comparison with the controls | | |
|---|---|---|---|
| | Dose mg/kg per os | | |
| | 200 | 100 | 50 |
| PIRACETAM | 20 | 48* | 10 |

*Values statistically different in comparison with controls.

Conclusion:

The products of exampls 4, 6 and 12 have shown an anti-amnesic activity at doses between 50 and 200 mg/kg.

What is claimed is:

1. Compounds of the formula (I):

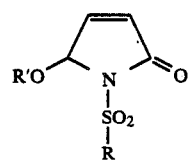

in which R' represents hydrogen, a linear, branched or cyclic alkyl containing up to 8 carbon atoms, alkenyl containing from 2 to 8 carbon atoms, acetyl, propionyl, butyryl or aralkyl containing from 7 to 15 carbon atoms and R represents phenyl, possibly substituted by the free, esterified or etherified hydroxy radical in which the ester or ether part has from 1 to 18 carbon atoms, the ketone and oxime functions, linear, branched or cyclic, alkyl or alkenyl having up to 18 carbon atoms, halogen, CF$_3$, SCF$_3$, OCF$_3$, NO$_2$, NH$_2$, C≡N, phenyl or alkoxycarbonyl containing from 2 to 8 carbon atoms and alkylsulphonyl containing 1 to 6 carbon atoms.

2. Compounds of the formula (I) as defined in claim 1, in which R represents possibly substituted phenyl.

3. Compounds of the formula (I) as defined in claim 1 or 2, in which R' represents a linear, branched or cyclic alkyl containing up to 8 carbon atoms.

4. Compounds of the formula (I) as defined in claim 3, in which R' represents n-butyl or n-pentyl.

5. Compounds as defined in claim 4, selected from the group consisting of 1-benzenesulphonyl-1,5-dihydro-5-n-butoxy-2H-pyrrol-2-one, 1-benzenesulphonyl-1,5-dihydro-5-n-pentyloxy-2H-pyrrol-2-one, and 1-(3-trifluoromethyl-benzenesulphonyl)-1,5-dihydro-5-n-butoxy-2H-pyrrol-2-one.

6. A therapeutic composition comprising a therapeutically effective amount of a compound as defined in any one of claims 1, 2, 4 or 5, and a pharmaceutically acceptable carrier.

7. A therapeutic composition comprising a therapeutically effective amount of a compound as defined in claim 3, and a pharmaceutically acceptable carrier.

* * * * *